US012611806B2

(12) United States Patent
Haverinen et al.

(10) Patent No.: US 12,611,806 B2
(45) Date of Patent: Apr. 28, 2026

(54) TECHNIQUES FOR MANUFACTURING A WEARABLE RING DEVICE

(71) Applicant: Oura Health Oy, Oulu (FI)

(72) Inventors: Teemu Juhani Haverinen, Oulu (FI);
Kari Kuisma Kanniainen, Ii (FI);
Marko Uusitalo, Oulu (FI); **Jouni
Juhani Huopana**, Oulu (FI)

(73) Assignee: Oura Health Oy, Oulu (FI)

( * ) Notice: Subject to any disclaimer, the term of this
patent is extended or adjusted under 35
U.S.C. 154(b) by 294 days.

(21) Appl. No.: 18/478,725

(22) Filed: Sep. 29, 2023

(65) Prior Publication Data

US 2025/0108545 A1 Apr. 3, 2025

(51) Int. Cl.
B29C 45/14 (2006.01)
A44C 9/00 (2006.01)
(Continued)

(52) U.S. Cl.
CPC ........ B29C 45/1459 (2013.01); A44C 9/0053
(2013.01); A61B 5/681 (2013.01); **B29C
45/0053 (2013.01); B29C 45/14344** (2013.01);
B29C 45/14598 (2013.01); B29C 45/14639
(2013.01); B29D 99/0082 (2013.01); **G06F
1/163 (2013.01); A44C 27/00 (2013.01); B29C
2045/0079 (2013.01); B29K 2063/00**
(2013.01); B29K 2995/0026 (2013.01); **B29L
2031/34 (2013.01); B29L 2031/48** (2013.01);
B29L 2031/7096 (2013.01); G06F 1/1656
(2013.01)

(58) Field of Classification Search
CPC .......................... B29C 45/1459; A44B 9/0053
See application file for complete search history.

(56) References Cited

U.S. PATENT DOCUMENTS

| | | | | |
|---|---|---|---|---|
| 4,109,343 A | * | 8/1978 | Weis | F16C 13/006 |
| | | | | 16/98 |
| 6,319,448 B1 | * | 11/2001 | Kirchdoerffer | G01K 13/25 |
| | | | | 264/272.17 |

(Continued)

FOREIGN PATENT DOCUMENTS

| | | | | | |
|---|---|---|---|---|---|
| CN | 104204830 B | * | 3/2018 | ............ | H02J 7/0069 |
| WO | 20120061438 A2 | | 5/2012 | | |

(Continued)

OTHER PUBLICATIONS

International Search Report and Written Opinion—PCT/US2023/
075706—SA/EPO—Apr. 26, 2024.

*Primary Examiner* — Benjamin A Schiffman
(74) *Attorney, Agent, or Firm* — ArentFox Schiff LLP

(57) ABSTRACT

Methods, systems, and devices for manufacturing a wearable ring device are described. A printed circuit board (PCB) may be connected to an inner cover, where one or more apertures of the inner cover are aligned with one or more sensors of the PCB. Additionally, an injection molding process may be performed to fill a cavity between the inner cover and a surface of one or more molds with a filler material. The filler material may bind the PCB to the inner cover and fill the one or more apertures with the filler material, creating a ring assembly. Following the injection molding process, an outer cover may be placed around the ring assembly and one or more side covers may engage to secure the inner cover to the outer cover.

19 Claims, 7 Drawing Sheets

(51) Int. Cl.

| | |
|---|---|
| *A61B 5/00* | (2006.01) |
| *B29C 45/00* | (2006.01) |
| *B29D 99/00* | (2010.01) |
| *B29L 31/48* | (2006.01) |
| *G06F 1/16* | (2006.01) |
| A44C 27/00 | (2006.01) |
| B29K 63/00 | (2006.01) |
| B29L 31/00 | (2006.01) |
| B29L 31/34 | (2006.01) |

(56) References Cited

U.S. PATENT DOCUMENTS

| | | | | |
|---|---|---|---|---|
| 6,428,357 | B1 * | 8/2002 | Dolinshek | H01R 43/18 |
| | | | | 29/856 |
| 7,955,543 | B2 * | 6/2011 | Deininger | B29C 45/14065 |
| | | | | 264/279.1 |
| 8,845,363 | B2 * | 9/2014 | Ardisana | H01R 13/504 |
| | | | | 439/607.35 |
| 9,861,314 | B2 * | 1/2018 | Haverinen | A61B 5/6801 |
| 10,362,692 | B2 * | 7/2019 | Lv | H05K 3/284 |
| 11,467,667 | B2 * | 10/2022 | Novich | H04R 1/023 |
| 11,853,030 | B2 * | 12/2023 | Sanchez | B33Y 50/00 |
| 11,911,181 | B1 * | 2/2024 | Huttunen | A61B 5/14551 |
| 12,263,623 | B2 * | 4/2025 | Lämsä | B29C 45/14221 |
| 12,419,578 | B2 * | 9/2025 | Huttunen | A61B 5/02055 |
| 12,440,161 | B2 * | 10/2025 | Haverinen | G06F 1/163 |
| 2003/0116886 | A1 * | 6/2003 | Nakazawa | B29C 45/062 |
| | | | | 264/255 |
| 2009/0004557 | A1 * | 1/2009 | Lasarov | H01M 50/231 |
| | | | | 428/98 |
| 2012/0313272 | A1 * | 12/2012 | Fullam | B29C 45/1671 |
| | | | | 264/279.1 |
| 2012/0315382 | A1 * | 12/2012 | Drysdale | G06F 1/163 |
| | | | | 427/160 |
| 2015/0092360 | A1 | 4/2015 | Stillman et al. | |
| 2021/0089130 | A1 | 3/2021 | Novich et al. | |
| 2023/0079736 | A1 | 3/2023 | Mäkinen | |
| 2024/0081012 | A1 | 3/2024 | Haverinen et al. | |
| 2025/0025101 | A1 * | 1/2025 | Huttunen | B29C 66/24221 |
| 2025/0055293 | A1 * | 2/2025 | Hwang | H02J 7/0045 |
| 2025/0089863 | A1 * | 3/2025 | Haverinen | A61B 5/02438 |
| 2025/0090095 | A1 * | 3/2025 | Haverinen | A61B 5/02416 |
| 2025/0099036 | A1 * | 3/2025 | Huopana | A61B 5/6826 |
| 2025/0135689 | A1 * | 5/2025 | Lämsä | B29C 41/20 |
| 2025/0224767 | A1 * | 7/2025 | Haverinen | G06F 1/1698 |

FOREIGN PATENT DOCUMENTS

| | | | | |
|---|---|---|---|---|
| WO | 20120170107 | A1 | 12/2012 | |
| WO | WO-2023064411 | A1 * | 4/2023 | A61B 5/6826 |
| WO | WO-2025043015 | A1 * | 2/2025 | A61B 5/6826 |

* cited by examiner

Inner Mold 405

425

Ring Assembly 410

Inner Ring-Shaped
Housing 402

406

Inner Mold 405

PCB 404

410

Inner Mold Pin 415

Inner Mold
Assembly 420

Inner Mold Pin 415

400

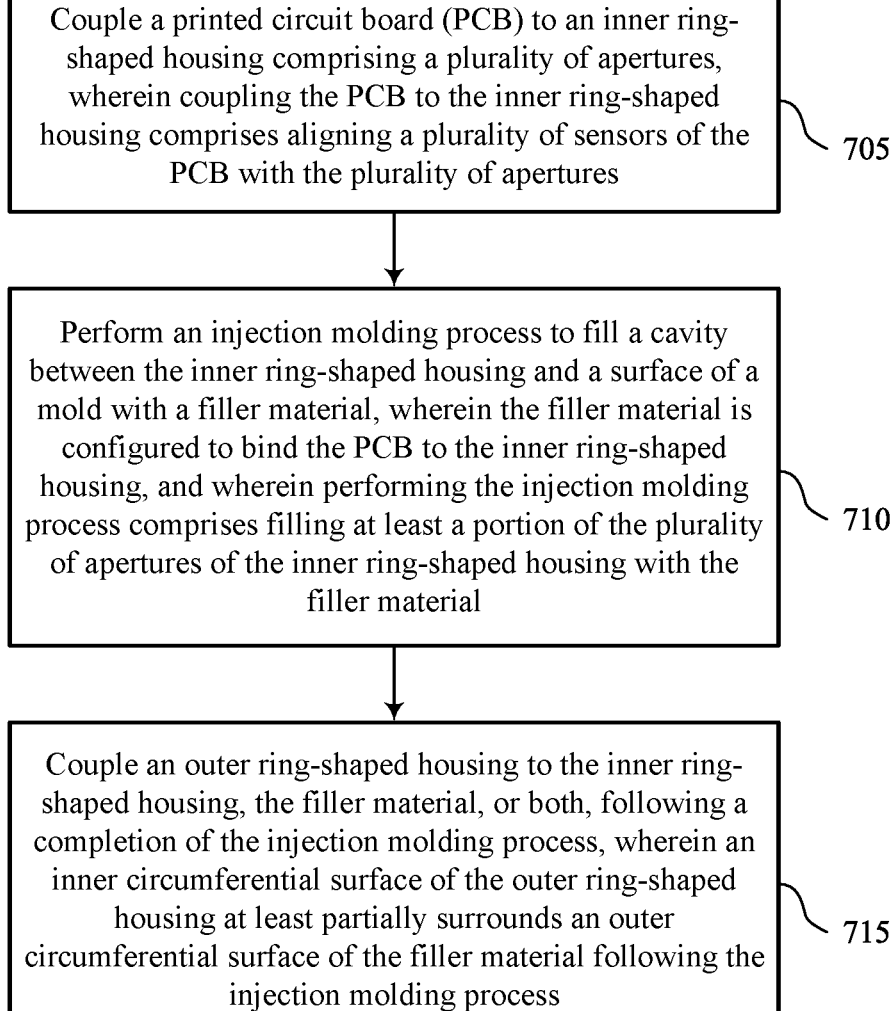

Couple a printed circuit board (PCB) to an inner ring-shaped housing comprising a plurality of apertures, wherein coupling the PCB to the inner ring-shaped housing comprises aligning a plurality of sensors of the PCB with the plurality of apertures    705

Perform an injection molding process to fill a cavity between the inner ring-shaped housing and a surface of a mold with a filler material, wherein the filler material is configured to bind the PCB to the inner ring-shaped housing, and wherein performing the injection molding process comprises filling at least a portion of the plurality of apertures of the inner ring-shaped housing with the filler material    710

Couple an outer ring-shaped housing to the inner ring-shaped housing, the filler material, or both, following a completion of the injection molding process, wherein an inner circumferential surface of the outer ring-shaped housing at least partially surrounds an outer circumferential surface of the filler material following the injection molding process    715

TECHNIQUES FOR MANUFACTURING A WEARABLE RING DEVICE

FIELD OF TECHNOLOGY

The following relates to wearable devices and data processing, including techniques for manufacturing a wearable ring device.

BACKGROUND

Some wearable devices may be configured to collect data from users to help the users understand more about their overall physiological health and well-being. However, manufacturing the wearable devices may be a complicated and expensive process and include vast room for human error.

BRIEF DESCRIPTION OF THE DRAWINGS

FIG. 7 shows a flowchart illustrating methods that support techniques for manufacturing a wearable ring device in accordance with aspects of the present disclosure.

DETAILED DESCRIPTION

Figure 1:
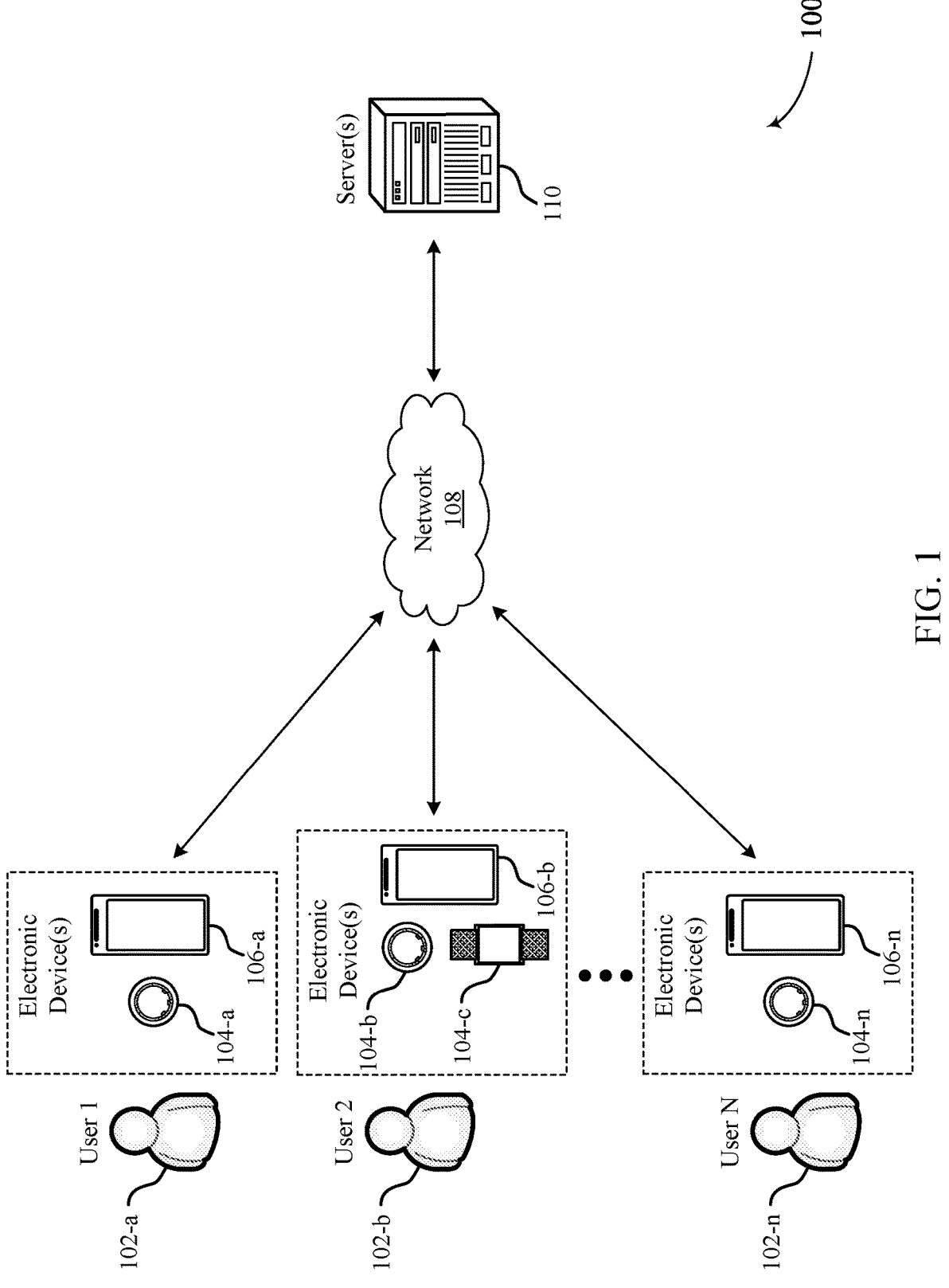
FIG. 1 illustrates an example of a system that supports techniques for manufacturing a wearable ring device in accordance with aspects of the present disclosure.

Some wearable ring devices may include an outer shell, and an epoxy inner shell. As such, manufacturing techniques for the wearable ring devices may manufacture the wearable ring device from the "outside in." For example, electrical components of the wearable ring device, such as a printed circuit board (PCB) and one or more optical sensors, are assembled within an outer cover, or shell, and secured with an inner epoxy cover, or shell, to form the wearable ring device. That is, the outer cover, with the electrical components, may be placed into a mold, and the inner epoxy cover may be formed to the other cover via injection molding. However, such manufacturing techniques suffer from several shortfalls. For instance, "outside in" manufacturing techniques may require tedious manual alignment of the optical components of the PCB within the mold by operators, including careful, tedious alignment for the inner epoxy molding. Specifically, operators have to manually align the optical components of the PCB, which is connected to the outer cover, within the mold to ensure that epoxy "domes" formed during the epoxy molding process are aligned with the optical components. This process may be tedious, time consuming, and place large amounts of pressure on the operators during the manufacturing process. Additionally, because the epoxy molding step is performed last, different gates (e.g., fill gates and vent gates) for the epoxy molding (e.g., gates where epoxy is inputted to fill the mold, and overflows out of) may be visible on the inside surface of the ring. As such, imperfections created from the fill/vent gates must be carefully polished to make the inner epoxy smooth and aesthetically pleasing. This polishing may be time consuming, and risk damaging the wearable ring device. Further, because the wearable ring device is manufactured "outside-in," each time a new outer cover is to be produced (e.g., a decorative or protective outer cover), the mold for the inner epoxy molding process has to be changed to fit the new outer shell. Changing the inner epoxy molding may lead to increased latency with creating new covers, and complications with forming partnerships with other entities.

Accordingly, techniques described herein may support a manufacturing process for wearable ring device that may be manufactured "inside out" (e.g., from an inner cover to an outer cover). Specifically, the electrical components (e.g., the PCB and one or more optical sensors) may be attached to an inner shell of the wearable ring device. Subsequently, the inner shell (e.g., and the attached electrical components) may be placed into a mold, such that a clear epoxy may be injection molded to secure the electrical components to the inner shell. The injection molding may further fill one or more apertures of the inner shell with the clear epoxy, such that the one or more optical sensors may be secured with relation to the one or more apertures to enable data collections. The result of injection molding the inner shell to the electrical components may be referred to as an inner cover, or a ring engine assembly that is essentially an operational ring (e.g., optical components, waterproof, etc.) without the outer cover. Subsequently, different outer covers may be slid around the inner cover and may be secured to the inner cover using side covers, to finish the ring.

The "inside out" manufacturing process described may address some of the shortfalls of previous approaches. For example, one or more locking features on the electrical components and inner shell may ensure an accurate alignment between the electrical components and the inner shell. As such, the orientation between the electrical components and the inner shell may not matter during the injection molding process, thereby alleviating the tedious manual alignment performed by operators during previous manufacturing processes (e.g., an "outside in" manufacturing process). Additionally, or alternatively, imperfections resulting from the gates (e.g., fill gates and vent gates) used in the molding step may be covered once the outer cover is put into position, thereby eliminating the need to polish such imperfections. Additionally, or alternatively, because the outer cover is installed last, the process for designing and manufacturing new outer cover (e.g., such as decorative or protective covers) may be greatly simplified. For instance, the creation of a new outer cover may no longer require custom molds to be made, as long as the new outer cover is able to slide around the ring engine assembly to finish the ring.

Aspects of the disclosure are initially described in the context of systems supporting physiological data collection from users via wearable devices. Aspects of the disclosure are further illustrated in cross-sectional views of a wearable ring device. Aspects of the disclosure are further illustrated by and described with reference to apparatus diagrams, system diagrams, and flowcharts that relate to techniques for manufacturing a wearable ring device.

FIG. 1 illustrates an example of a system 100 that supports techniques for manufacturing a wearable ring device in accordance with aspects of the present disclosure. The system 100 includes a plurality of electronic devices (e.g., wearable devices 104, user devices 106) that may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, that may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators.

Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, heart rate variability (HRV), actigraphy, galvanic skin response, pulse oximetry, blood oxygen saturation (SpO2), blood sugar levels (e.g., glucose metrics), and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some of which may measure physiological parameters and some of which may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-a (User 1) may operate, or may be associated with, a wearable device 104-a (e.g., ring 104-a) and a user device 106-a that may operate as described herein. In this example, the user device 106-a associated with user 102-a may process/store physiological parameters measured by the ring 104-a. Comparatively, a second user 102-b (User 2) may be associated with a ring 104-b, a watch wearable device 104-c (e.g., watch 104-c), and a user device 106-b, where the user device 106-b associated with user 102-b may process/store physiological parameters measured by the ring 104-b and/or the watch 104-c. Moreover, an nth user 102-n (User N) may be associated with an arrangement of electronic devices described herein (e.g., ring 104-n, user device 106-n). In some aspects, wearable devices 104 (e.g., rings 104, watches 104) and other electronic devices may be communicatively coupled to the user devices 106 of the respective users 102 via Bluetooth, Wi-Fi, and other wireless protocols.

In some implementations, the rings 104 (e.g., wearable devices 104) of the system 100 may be configured to collect physiological data from the respective users 102 based on arterial blood flow within the user's finger. In particular, a ring 104 may utilize one or more light-emitting components, such as LEDs (e.g., red LEDs, green LEDs) that emit light on the palm-side of a user's finger to collect physiological data based on arterial blood flow within the user's finger. In general, the terms light-emitting components, light-emitting elements, and like terms, may include, but are not limited to, LEDs, micro LEDs, mini LEDs, laser diodes (LDs) (e.g., vertical cavity surface-emitting lasers (VCSELs), and the like.

In some cases, the system 100 may be configured to collect physiological data from the respective users 102 based on blood flow diffused into a microvascular bed of skin with capillaries and arterioles. For example, the system 100 may collect PPG data based on a measured amount of blood diffused into the microvascular system of capillaries and arterioles. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices that utilize LEDs that are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data.

The electronic devices of the system 100 (e.g., user devices 106, wearable devices 104) may be communicatively coupled to one or more servers 110 via a wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the ring 104-a associated with the first user 102-a may be communicatively coupled to the user device 106-a, where the user device 106-a is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time that a user 102 is asleep, and classify periods of time that the user 102 is asleep into one or more sleep stages (e.g., sleep stage classification). For example, as shown in FIG. 1, User 102-a may be associated with a wearable device 104-a (e.g., ring 104-a) and a user device 106-a. In this example, the ring 104-a may collect physiological data associated with the user 102-a, including temperature, heart rate, HRV, respiratory rate, and the like. In some aspects, data collected by the ring 104-a may be input to a machine learning classifier, where the machine learning classifier is configured to determine periods of time that the user 102-a is (or was) asleep. Moreover, the machine learning classifier may be configured to classify periods of time into different sleep stages, including an awake sleep stage, a rapid eye movement (REM) sleep stage, a light sleep stage (non-REM (NREM)), and a deep sleep stage (NREM). In some aspects, the classified sleep stages may be displayed to the user 102-a via a GUI of the user device 106-a. Sleep stage classification may be used to provide feedback to a user 102-a regarding the user's sleeping patterns, such as recommended bedtimes, recommended wake-up times, and the like. Moreover, in some implementations, sleep stage classification techniques described herein may be used to calculate scores for the respective user, such as Sleep Scores, Readiness Scores, and the like.

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle, that repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-a via the wearable device 104-a. In this example, the circadian rhythm adjustment model may be configured to "weight," or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models that are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state: 2) circadian rhythms: 3) non-endogenous daily rhythms shown to be imposed on top of circadian rhythms, as in work schedules: 4) weekly rhythms, or other artificial time periodicities exogenously imposed (e.g., in a hypothetical culture with 12 day "weeks," 12 day rhythms could be used): 5) multi-day ovarian rhythms in women and spermatogenesis rhythms in men: 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

In some aspects, the respective devices of the system 100 may be manufactured according to the techniques described herein. For example, each ring 104 may include an inner cover and an outer cover. In some cases, electrical components (e.g., PCB, optical sensors, etc.) may be secured or otherwise attached to the inner cover/shell of the ring, where the inner cover/shell and the electrical components may collectively be referred to as a "ring engine assembly," which may essentially be a completed ring 104 without an outer cover. In some cases, the electrical components may be secured to the inner metal shell via injection molding using a clear epoxy, thereby forming the ring engine assembly. Subsequently, the outer cover may be placed, or slid, around the inner cover and side covers (e.g., ring-shaped fittings) may be placed on each side of the ring 104, aligning with respective slots between the outer cover and the inner cover on each side of the ring 104.

As such, the ring 104 may be manufactured "inside out" (e.g., from an inner cover to an outer cover). The injection molding may fill one or more apertures of the inner shell with the clear epoxy, such that the one or more optical sensors may be secured with relation to the one or more apertures to enable data collections. Additionally, different outer covers may be slid around the inner cover and may be secured to the inner cover using side covers, to finish the ring.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
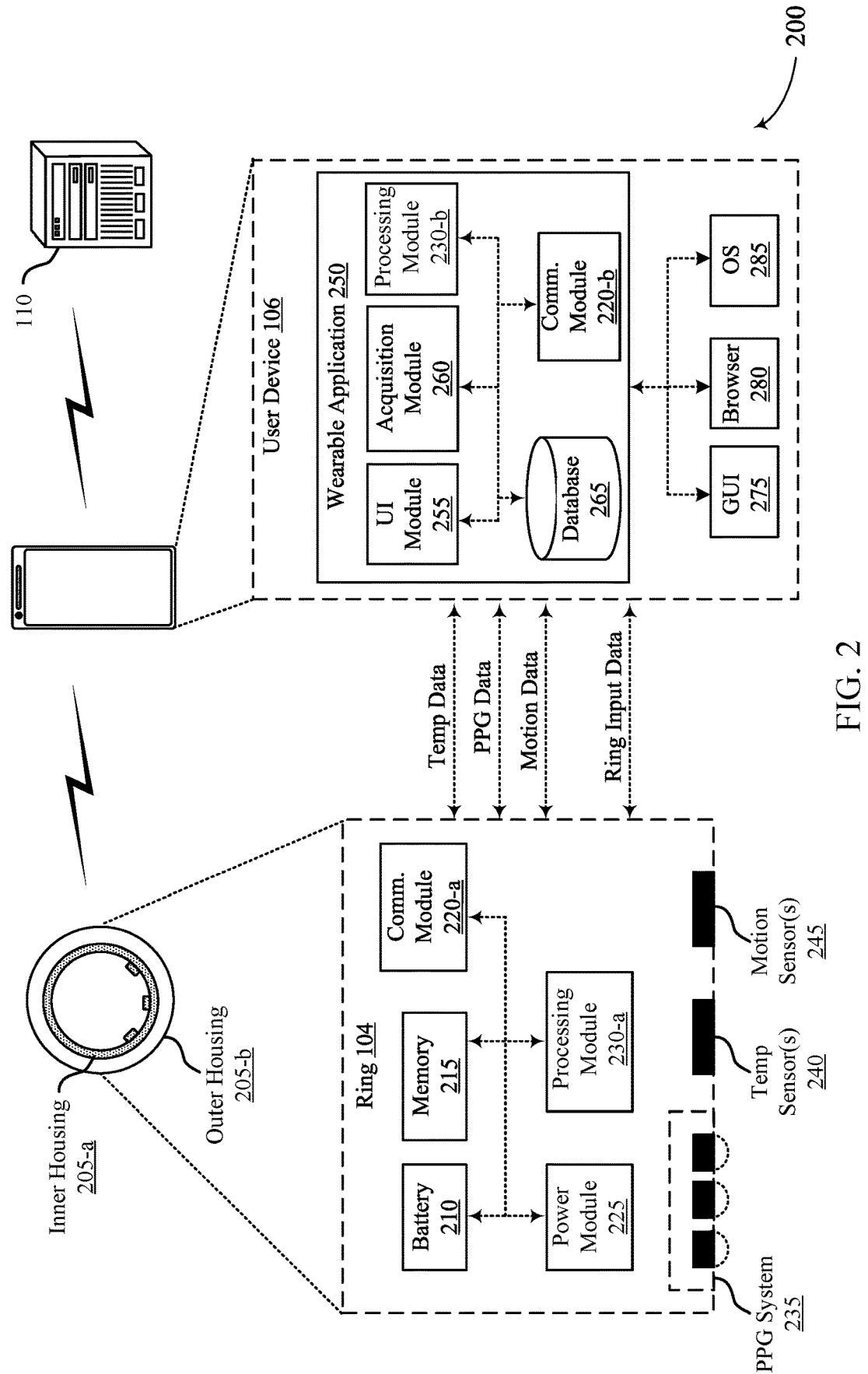
FIG. 2 illustrates an example of a system that supports techniques for manufacturing a wearable ring device in accordance with aspects of the present disclosure.

FIG. 2 illustrates an example of a system 200 that supports techniques for manufacturing a wearable ring device in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels (SpO2), blood sugar levels (e.g., glucose metrics), and the like.

The system 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, photoplethysmogram (PPG) data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205 that may include an inner housing 205-*a* and an outer housing 205-*b*. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-*a*, a memory 215, a communication module 220-*a*, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components that are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using adhesives, wraps, clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-*b* component (e.g., a shell) and an inner housing 205-*a* component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-*b* (e.g., a metal outer housing 205-*b*). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate(s) from water and/or other chemicals.

The outer housing 205-*b* may be fabricated from one or more materials. In some implementations, the outer housing 205-*b* may include a metal, such as titanium, that may provide strength and abrasion resistance at a relatively light weight. The outer housing 205-*b* may also be fabricated from other materials, such polymers. In some implementations, the outer housing 205-*b* may be protective as well as decorative.

The inner housing 205-*a* may be configured to interface with the user's finger. The inner housing 205-*a* may be formed from a polymer (e.g., a medical grade polymer) or other material. In some implementations, the inner housing 205-*a* may be transparent. For example, the inner housing 205-*a* may be transparent to light emitted by the PPG light emitting diodes (LEDs). In some implementations, the inner housing 205-*a* component may be molded onto the outer housing 205-*b*. For example, the inner housing 205-*a* may include a polymer that is molded (e.g., injection molded) to fit into an outer housing 205-*b* metallic shell.

The ring 104 may include one or more substrates (not illustrated). The device electronics and battery 210 may be included on the one or more substrates. For example, the device electronics and battery 210 may be mounted on one or more substrates. Example substrates may include one or more printed circuit boards (PCBs), such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-*a* of the ring 104 may include one or more processors (e.g., processing units), microcontrollers, digital signal processors, systems on a chip (SOCs), and/or other processing devices. The processing module 230-*a* communicates with the modules included in the ring 104. For example, the processing module 230-*a* may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-*a* may communicate with the memory 215. The memory 215 may include computer-readable instructions that, when executed by the processing module 230-*a*, cause the processing module 230-*a* to perform the various functions attributed to the processing module 230-*a* herein. In some implementations, the processing module 230-*a* (e.g., a microcontroller) may include additional features associated with other modules, such as communication functionality provided by the communication module 220-*a* (e.g., an integrated Bluetooth Low Energy transceiver) and/or additional onboard memory 215.

The communication module 220-*a* may include circuits that provide wireless and/or wired communication with the user device 106 (e.g., communication module 220-*b* of the user device 106). In some implementations, the communication modules 220-*a*, 220-*b* may include wireless communication circuits, such as Bluetooth circuits and/or Wi-Fi circuits. In some implementations, the communication modules 220-*a*. 220-*b* can include wired communication circuits, such as Universal Serial Bus (USB) communication circuits. Using the communication module 220-*a*, the ring 104 and the user device 106 may be configured to communicate with each other. The processing module 230-*a* of the ring may be configured to transmit/receive data to/from the user device 106 via the communication module 220-*a*. Example data may include, but is not limited to, motion data, temperature data, pulse waveforms, heart rate data, HRV data, PPG data, and status updates (e.g., charging status, battery charge level, and/or ring 104 configuration settings). The processing module 230-*a* of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors that may be used to collect data in addition to, or that supplements, data collected by the ring 104 itself. Moreover, a charger or other power source for the ring 104 may function as a user device 106, in which case the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during charging. The power module 225 may also regulate voltage(s) of the device electronics, regulate power output to the device electronics, and monitor the state of charge of the battery 210. In some implementations, the battery 210 may include a protection circuit module (PCM) that protects the battery 210 from high current discharge, over voltage during charging, and under voltage during discharge. The power module 225 may also include electro-static discharge (ESD) protection.

The one or more temperature sensors 240 may be electrically coupled to the processing module 230-*a*. The temperature sensor 240 may be configured to generate a temperature signal (e.g., temperature data) that indicates a temperature read or sensed by the temperature sensor 240. The processing module 230-*a* may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-*a*) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-*a* may use to determine the temperature. As another example, in cases where the temperature sensor 240 includes a passive sensor, the processing module 230-*a* (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-*a* may sample the user's temperature over time. For example, the processing module 230-*a* may sample the user's temperature according to a sampling rate. An example sampling rate may include one sample per second, although the processing module 230-*a* may be configured to sample the temperature signal at other sampling rates that are higher or lower than one sample per second. In some implementations, the processing module 230-*a* may sample the user's temperature continuously throughout the day and night. Sampling at a sufficient rate (e.g., one sample per second) throughout the day may provide sufficient temperature data for analysis described herein.

The processing module 230-*a* may store the sampled temperature data in memory 215. In some implementations, the processing module 230-*a* may process the sampled temperature data. For example, the processing module 230-*a* may determine average temperature values over a period of time. In one example, the processing module 230-*a* may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate, which may be stored in memory 215, may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-*a* near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-*a* may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-*a* may sample the sensors at different rates and average/store different values for the different sensors. In some implementations, the processing module 230-*a* may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-*a* may sample the PPG signal and determine a user's pulse waveform based on the PPG signal. The processing module 230-*a* may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 where the optical receiver(s) receive transmitted light that is reflected through the region of the user's finger. In some implementations, the PPG system 235 may be configured as a transmissive PPG system 235 where the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include light-emitting diodes (LEDs). The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-*a* may control one or both of the optical transmitters to transmit light while sampling the PPG signal generated by the optical receiver. In some implementations, the processing module 230-*a* may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform that may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-*a* may store the pulse waveform in memory 215 in some implementations. The processing module 230-*a* may process the pulse waveform as it is generated and/or from memory 215 to determine user physiological parameters described herein.

The processing module 230-*a* may determine the user's heart rate based on the pulse waveform. For example, the processing module 230-*a* may determine heart rate (e.g., in beats per minute) based on the time between peaks in the pulse waveform. The time between peaks may be referred to as an interbeat interval (IBI). The processing module 230-*a* may store the determined heart rate values and IBI values in memory 215.

The processing module 230-*a* may determine HRV over time. For example, the processing module 230-*a* may determine HRV based on the variation in the IBIs. The processing module 230-*a* may store the HRV values over time in the memory 215. Moreover, the processing module 230-*a* may determine the user's respiratory rate over time. For example, the processing module 230-*a* may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-*a* may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers.

As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BMI160 inertial micro electro-mechanical system (MEMS) sensor that may measure angular rates and accelerations in three perpendicular axes.

The processing module 230-a may sample the motion signals at a sampling rate (e.g., 50 Hz) and determine the motion of the ring 104 based on the sampled motion signals. For example, the processing module 230-a may sample acceleration signals to determine acceleration of the ring 104. As another example, the processing module 230-a may sample a gyro signal to determine angular motion. In some implementations, the processing module 230-a may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a Sleep Score), activity metrics, and readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-a may compress the data stored in memory 215. For example, the processing module 230-a may delete sampled data after making calculations based on the sampled data. As another example, the processing module 230-a may average data over longer periods of time in order to reduce the number of stored values. In a specific example, if average temperatures for a user over one minute are stored in memory 215, the processing module 230-a may calculate average temperatures over a five minute time period for storage, and then subsequently erase the one minute average temperature data. The processing module 230-a may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS), a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., "app") that may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-b, a communication module 220-b, and a storage module (e.g., database 265) configured to store application data.

The various data processing operations described herein may be performed by the ring 104, the user device 106, the servers 110, or any combination thereof. For example, in some cases, data collected by the ring 104 may be preprocessed and transmitted to the user device 106. In this example, the user device 106 may perform some data processing operations on the received data, may transmit the data to the servers 110 for data processing, or both. For instance, in some cases, the user device 106 may perform processing operations that require relatively low processing power and/or operations that require a relatively low latency, whereas the user device 106 may transmit the data to the servers 110 for processing operations that require relatively high processing power and/or operations that may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., Sleep Score, Readiness Score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, Sleep Scores, Readiness Scores, and the like.

In some cases, "sleep days" may align with the traditional calendar days, such that a given sleep day runs from midnight to midnight of the respective calendar day. In other cases, sleep days may be offset relative to calendar days. For example, sleep days may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner that is consistent with their sleep schedules. In some cases, users may be able to selectively adjust (e.g., via the GUI) a timing of sleep days relative to calendar days so that the sleep days are aligned with the duration of time that the respective users typically sleep.

In some implementations, each overall score for a user for each respective day (e.g., Sleep Score, Readiness Score) may be determined/calculated based on one or more "contributors," "factors," or "contributing factors." For example, a user's overall Sleep Score may be calculated based on a set of contributors, including: total sleep, efficiency, restfulness, REM sleep, deep sleep, latency, timing, or any combination thereof. The Sleep Score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall Readiness Score may be calculated based on a set of contributors, including: sleep, sleep balance, heart rate, HRV balance, recovery index, temperature, activity, activity balance, or any combination thereof. The Readiness Score may include any quantity of contributors. The "sleep" contributor may refer to the combined Sleep Score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the Readiness Score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

In some aspects, the system 200 may support techniques for manufacturing the ring 104 in accordance with the techniques described herein. For example, electrical components of the ring 104, such as the battery 210, the memory

215, the communication module 220-*a*, the power module 225, the processing module 230-*a*, the PPG system 235, the temperature sensor(s) 240, the motion sensor(s) 245, or any combination thereof, may be attached to an inner cover, or shell. The inner cover/shell may be manufactured from metal materials, plastic materials, epoxy materials, and the like. Additionally, the inner metal cover, attached to the electrical components, may be placed in a mold, such that a clear epoxy can be injection molded to secure the electrical components to the inner cover. The injection molding may further fill one or more apertures of the inner cover with the clear epoxy, such that the one or more optical sensors, such as the PPG system 235, may be secured with relation to the one or more apertures to enable data collection through the one or more apertures. The result of injection molding the inner cover to the electrical components may be referred to as the inner housing 205-*a*, or engine assembly, of the ring 104. The engine assembly may be an operational ring 104 without the outer housing 205-*b*.

Subsequently, the outer housing 205-*b* (e.g., an outer cover) may be slid, or placed, around the inner housing 205-*a* and may be secured to the inner housing 205-*a* using side covers (e.g., ring-shaped fittings). That is, side covers may be placed on each side of the ring 104, aligning with respective slots between the outer housing 205-*b* and the inner housing 205-*a* on each side of the ring 104. The outer housing 205-*b* (e.g., outer cover/shell) may be manufactured from the same or different material(s) as compared to the inner housing 205-*a*, such as a metal material, an epoxy material, a plastic material, a rubber material, etc.

Figure 3:
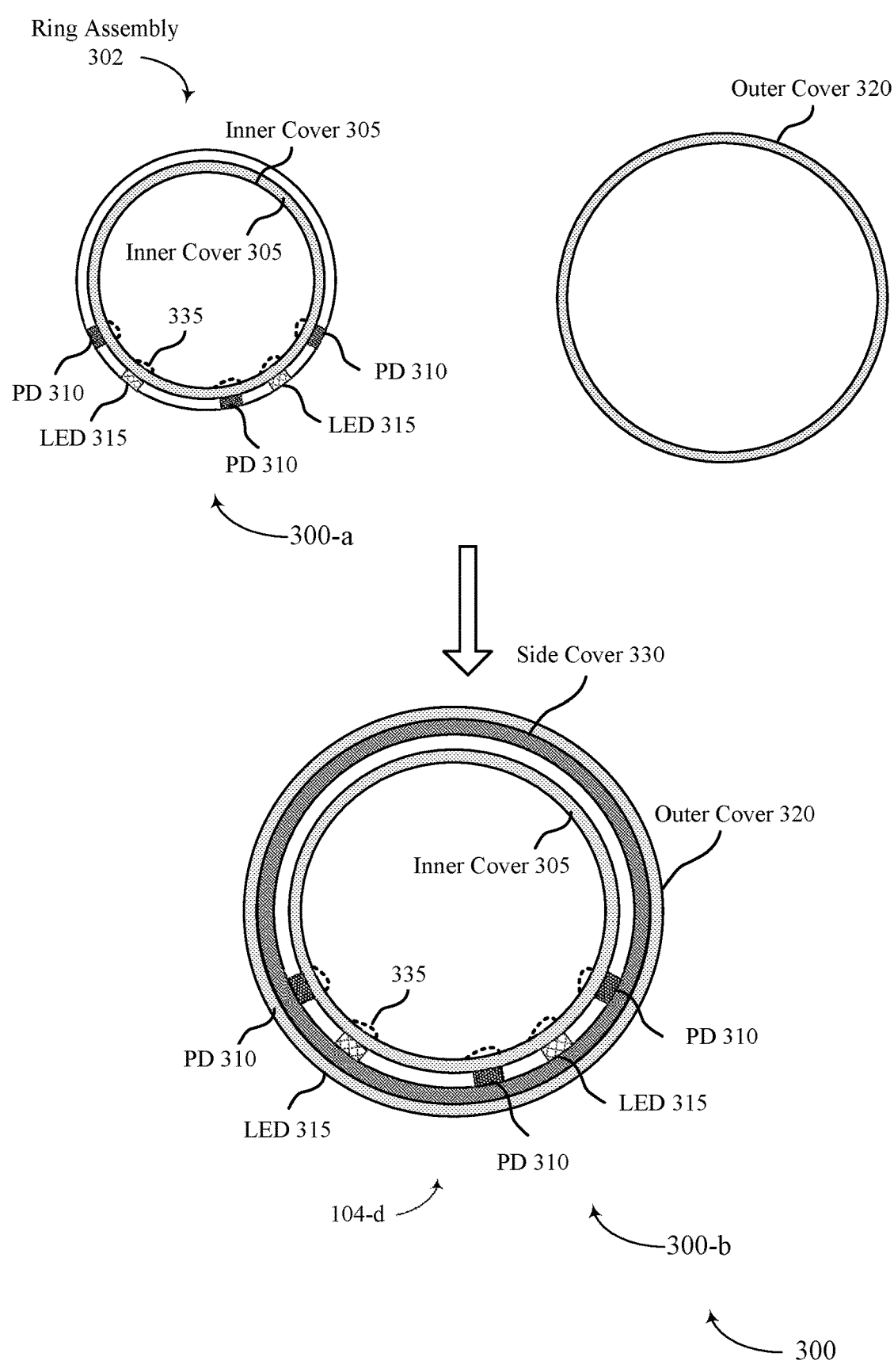
FIG. 3 shows example cross-sectional views of a wearable ring device that supports techniques for manufacturing a wearable ring device in accordance with aspects of the present disclosure.

FIG. 3 shows examples of a wearable device diagram 300 that supports techniques for manufacturing a wearable ring device in accordance with aspects of the present disclosure. The wearable device diagram 300 may implement, or be implemented by, aspects of the system 100, the system 200, or both. For example, the wearable device diagram 300 may include a wearable ring device 104-*d*, which may be an example of wearable devices 104 as described with reference to FIG. 1. As an illustrative example, the wearable device diagram 300 may include cross sectional views (e.g., a cross-sectional view 300-*a* and a cross-sectional view 300-*b*) of different portions of a ring 104 (e.g., the wearable ring device 104-*d*). Although the wearable devices are illustrated as circular in FIG. 3, they may be any shape and any example of a wearable device (e.g., a ring, a watch or wristband, an armband, a necklace, and the like).

Specifically, the wearable ring device 104-*d* of the wearable device diagram 300 (e.g., illustrated by the cross-sectional view 300-*b*) may illustrate a completed ring 104 (e.g., a ring 104 that has undergone the "inside out" manufacturing process). For example, the wearable ring device 104-*d* may include at least an inner cover 305, one or more electrical components (e.g., one or more PDs 310, one or more LEDs 315, etc.), an outer cover 320, an epoxy layer 325, and one or more side covers 330. Additionally, or alternatively, the "inside out" manufacturing process may create a ring engine assembly or "ring assembly 302" (e.g., illustrated by the cross-sectional view 300-*a*) that serves as an operational ring 104 (e.g., includes the necessary optical components, waterproof, etc.) without the need of the outer cover 320.

In some cases, the wearable device 104-*d* may include an electronic substrate, such as a printed wiring board (PWB) or PCB. The electronic substrate may be attached (e.g., coupled) to the inner cover 305. The inner cover 305 (e.g., an inner ring-shaped housing) may be an inner metallic shell and include one or more apertures. In such cases, the respective electronic substrates may include or may be connected (e.g., communicatively coupled) to sensors disposed on/within the ring assembly 302. That is, the "inside out" manufacturing method may include aligning the sensors of the PCB with the apertures. Additionally, or alternatively, the PCB may include a set (e.g., a first set) of locating components and the inner cover 305 may include a set (e.g., a second set) of locating components that help maintain the PCB in alignment (e.g., in a radial orientation) with the apertures.

For the purposes of the present disclosure, the term "sensor" may be used to refer to a module including a pair of light-emitting and light-receiving components, such as one or more LEDs 315 and one or more PDs 310. Moreover, the light-emitting component and light-receiving component of a "sensor" may be co-located (e.g., positioned within the same sensor housing) and/or may be positioned at different locations on/within the ring assembly 302. Additionally, in some cases, a "sensor" may include other components in addition to the LEDs 315 and the PDs 310, such as lenses.

In some cases, the wearable device may be manufactured by performing an injection molding process. For example, the inner cover 305 may be placed into a mold, and a filler may be injected into the mold such that the electrical components of the ring 104 are secured to the inner cover 305 via the filler material. Additionally, injecting filler into the mold may result in the filler material filling one or more apertures of the inner cover 305, such that the one or more optical sensors, aligned with the apertures, may collect data (e.g., physiological data) via transmission of signaling (e.g., light) through the apertures.

In some cases, the injection molding process may form the ring assembly 302 that includes an epoxy layer 325 (e.g., made up of the filler material) surrounding the inner cover 305 (e.g., an inner circumferential surface). That is, the epoxy layer/filler material may be used to secure the LEDs 315 and PDs 310 (and other sensors/components of the device) to the inner cover 305. Thus, the component produced as a result of the injection molding process (e.g., the inner cover 305 molded to the electoral components via the filler) may be referred to as the ring assembly (e.g., ring engine assembly). In some cases, the ring assembly 302 may essentially be an operational wearable device, where the epoxy material/filler material creates a watertight seal around the sensors of the device.

In some implementations, as further described herein, the injection molding process may additionally or alternatively be used to form domes 335 over the optical components (e.g., LEDs 315, PDs 310) of the inner cover 305 of the ring assembly 302. That is, the LEDs 315 and PDs 310 may be disposed within, or otherwise aligned with, apertures within the inner cover 305, where the domes 335 may substantially cover and/or fill the apertures. It has been found that such domes 335 that cover the apertures may result in better contact with a tissue of the user's skin, thereby improving the quality of collected physiological data collected by the wearable ring device 104. The domes 335 may be formed to be curved (e.g., spherical-shaped, elliptical-shaped), multi-faceted, or both.

In some cases, the outer cover 320 may be slid around the ring assembly 302. The outer cover 320 may be an outer metallic shell that is a same or different material then the inner cover 305. For instance, the inner cover 305 may be manufactured from titanium (e.g., a titanium inlet ring), while the outer cover 320 may be manufactured from steel. In some cases, side covers 330 may be used to secure the outer cover 320 to the inner cover 305. For example, a first side cover 330 and a second side cover 330 may fill gaps between the outer cover 320 and the inner cover 305 on a first lateral side and a second lateral side of the wearable ring device, respectively. In some cases, as will be described in further detail herein, the outer cover 320 may be interchangeable, such that the user is able to swap out different outer covers 320 to change the functionality and/or aesthetic appearance of the ring.

Figure 4:
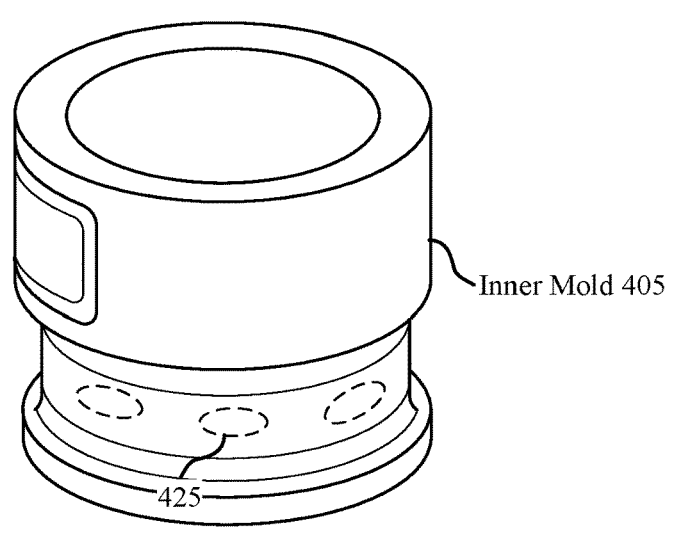
FIG. 4 shows an example of a system that supports techniques for manufacturing a wearable ring device in accordance with aspects of the present disclosure.

FIG. 4 shows an example of a system 400 that supports techniques for manufacturing a wearable ring device in accordance with aspects of the present disclosure. The system 400 may implement, or be implemented by, aspects of the system 100, the system 200, the wearable device diagram 300, or any combination thereof. Specifically, the system 400 may illustrate the different components of an inner mold assembly 420 that is used to manufacture a wearable ring device 104. For example, the inner mold assembly 420 may include one or more of an inner mold 405, a ring assembly 410, and an inner mold pin 415. In particular, the system 400 illustrated in FIG. 4 (as well as the system 500 illustrated in FIG. 5) may be used to perform a molding process that is used to create the ring assembly 410, which may be an example of the ring assembly 302 illustrated in FIG. 3.

When manufacturing the ring assembly 410 (e.g., ring assembly 302), a battery (e.g., of a ring 104) and/or PCB 404 may be attached to the inner cover (e.g., inner ring-shaped housing 402) of the wearable ring device, as shown in FIG. 4. In some cases, the PCB 404 may include one or more locating components or features that are configured to engage with one or more locating features of the inner ring-shaped housing 402 to ensure correct alignment between sensors (e.g., LEDs, photodetectors) of the PCB 404 and apertures 406 within the inner ring-shaped housing 402.

In some cases, the ring assembly 410 may represent the ring assembly (e.g., engine ring assembly) described in more detail with reference to FIG. 3. For example, the ring assembly 410 may include at least the inner ring-shaped housing 402 (e.g., the inner cover 305) and one or more electrical components (e.g., the one or more PDs 310, the one or more LEDs 315, etc.). Additionally, or alternatively, the ring assembly 410 may include at least a battery, one or more tapes (e.g., used to fix/restrain the positions of at least some components), or both.

Figure 5:
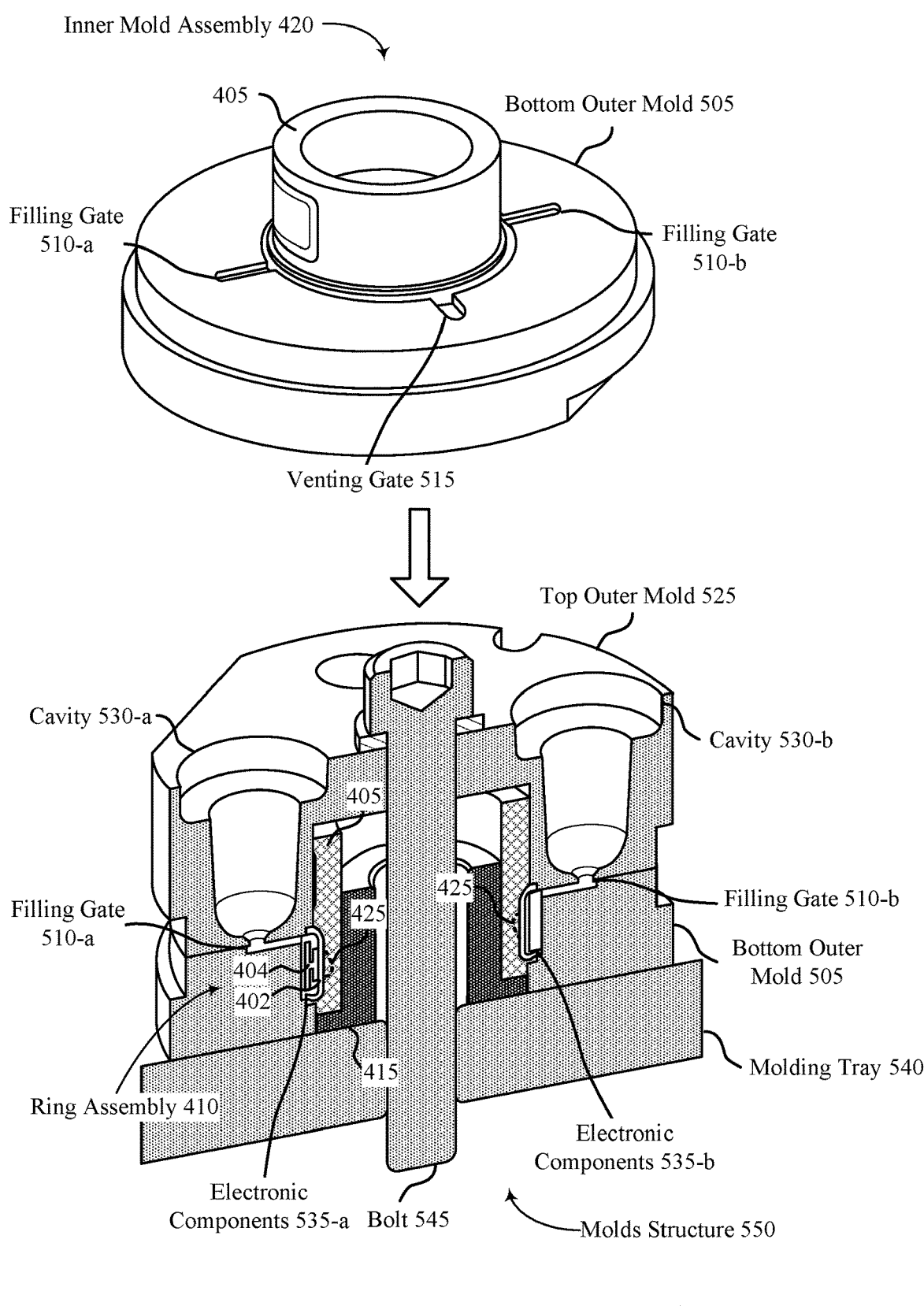
FIG. 5 shows an example of a system that supports techniques for manufacturing a wearable ring device in accordance with aspects of the present disclosure.

In some cases, the battery and/or PCB 404 may be attached to the inner ring-shaped housing 402 before the molding process shown and described in FIGS. 4 and 5. Subsequently, the injection molding process (shown in FIGS. 4 and 5) may bind the battery and PCB 404 to the inner ring-shaped housing 402. Thus, the filler material used during the molding process may be molded over the battery and/or PCB 404, thereby securing the battery and/or PCB 404 to the inner ring-shaped housing 402 of the ring assembly 410.

In some other cases, the molding process may be performed without the battery (e.g., before the battery is attached to the inner ring-shaped housing 402). In such cases, the PCB 404 may include electrical leads that extend out from the filler/epoxy material used to perform the molding process, where the electrical leads may be connected to the battery (such that the PCB 404 is disposed under/within the filler/epoxy material, and the battery is positioned on top of or outside the filler/epoxy material). In other words, the PCB 404 may have electrical leads that may electrically connect (e.g., couple) the battery with one or more electrical components (e.g., sensors) of the PCB 404.

The electrical leads may extend out from a cavity during the molding process such that the electrical leads extend from the filler material (e.g., the epoxy layer 325) after (e.g., following the completion of) the molding process. Such techniques may enable the battery to be easily replaced, as the battery would be located outside of the filler/epoxy material used during the molding process (e.g., the electrical leads may connect to the battery after the molding process). This concept will be further described herein.

After coupling the PCB 404 (and/or battery in some cases) to the inner ring-shaped housing 402, the ring assembly 410 may be placed onto the inner mold 405, as shown in FIG. 4. In some cases, the inner mold 405 may be made up of one or more materials including at least a hard metal material, plastic, thermoplastic elastomers (TPE), silicone, etc. For instance, the inner mold 405 may be made up of silicone or other TPE materials, such that the filling (e.g., epoxy) may not stick to the inner mold 405. The inner mold 405 may be used to create optical lenses (e.g., specified visual surface) of a wearable ring device 104.

In some implementations, the inner mold 405 may include one or more depressions 425 that are used to create epoxy "domes" (e.g., domes 335) on/within the inner ring-shaped housing 402 of the wearable ring device 104. In other words, the inner mold 405 may include one or more "Seeger" rings that include depressions 425 or indents that are used to create domes (e.g., domes 335) on/within the inner ring-shaped housing 402. In particular, in some cases, the ring assembly 410 may be placed on/around the inner mold 405 such that the apertures 406 within the inner ring-shaped housing 402 align with the depressions 425 within the inner mold 405. In this regard, when the injection molding process is performed, the epoxy/filler material may fill/cover the outer surface of the ring assembly 410, and flow out of the apertures 406 to fill the depressions 425, thereby creating "domes" that cover the apertures 406. Such domes (e.g., domes 335) that cover the apertures 406 may result in better contact with a tissue of the user's skin, thereby improving the quality of collected physiological data collected by the wearable ring device 104. The depressions 425 may be shaped to form any type or shape of dome 335, such as curved domes (e.g., spherical or elliptical-shaped depressions 425 to create spherical or elliptical-shaped domes 335), multi-faceted (e.g., multi-faceted depressions 425 to create multi-faceted domes 335), and the like.

Prior to performing the injection molding process, the inner mold pin 415 may be inserted into the inner mold 405 to form the inner mold assembly 420, as shown in FIG. 4. In some cases, the inner mold pin 415 may be made up of one or more materials including at least a hard metal material, plastic, TPE, silicone, etc. For example, the inner mold pin 415 may be made up of a metal, a plastic, or both, to create a compression to (e.g., against) the inner mold 405. In some instances, the inner mold pin 415 may be inserted into the inner mold 405 and the ring assembly 410 (e.g., the inner cover). The inner mold pin 415 may control an amount of filler material (e.g., epoxy) that flows out of a cavity through the apertures 406 of the inner ring-shaped housing 402 during the molding process. Additionally, or alternatively, the inner mold pin 415 may create a seal against the inner mold 405 (e.g., further sealing the inner mold assembly 420 against having metal inlet openings). For instance, the inner mold pin 415 may be substantially flush with the inner surface (inner circumferential surface) of the inner ring-shaped housing 402 of the ring assembly 410 (e.g., the inner cover) during the molding process. Thus, the filler material within the apertures 406 may also be substantially flush with the inner surface of the inner ring-shaped housing 402 after the molding process.

FIG. 5 shows an example of a system 500 that supports techniques for manufacturing a wearable ring device in accordance with aspects of the present disclosure. The system 500 may implement, or be implemented by, aspects of the system 100, the system 200, the wearable device diagram 300, the system 400, or any combination thereof. Specifically, the system 500 may illustrate the injection molding process of the "inside out" manufacturing process for a wearable ring device (e.g., the wearable device 104 and the wearable ring device 104-*d*, as described with reference to FIG. 1 and FIG. 3, respectively).

The system 500 illustrated in FIG. 5 further illustrates the steps/components of the molding process illustrated in FIG. 4 that is used to create the ring assembly 410, which may be an example of the ring assembly 302 illustrated in FIG. 4. In particular, the system 500 illustrates a continuation of the molding process illustrated in FIG. 4 where the ring assembly 410 is placed around the inner mold assembly 420 including the inner mold 405 and the inner mold pin 415.

Specifically, the system 500 may include a mold structure 550 with one or more molds. For example, a bottom outer mold 505 may at least partially surround (e.g., enclose) the inner mold assembly 420, as described with reference to FIG. 4. The bottom outer mold 505 may be made out of a hard metal material (e.g., steel). Additionally, or alternatively, the bottom outer mold 505 may include one or more gates (e.g., molding gates). These gates may allow the filler (e.g., transparent epoxy) to flow in, or out, of the bottom outer mold 505. For instance, the bottom outer mold 505 may include one or more filling gates 510 (e.g., a filling gate 510-*a* and a filling gate 510-*b*) and one or more venting gates 515. In some instances, Computer Numerical Control (CNC) manufacturing (e.g., machining) may help control a size and a shape for each gate, as well as any other aspect of the bottom outer mold 505. In some other instances, the molding gates may be made out of silicone molds. However, silicone molds may have tolerances that are harder to control, among other molding defects (e.g., flash and burrs that may drop the molding yield associated with the molding process output).

In some cases, the molds structure 550 may include a top outer mold 525. The top outer mold 525 may at least partially surround (e.g., enclose) the inner mold assembly 420. The top outer mold 525 may be located on top of the bottom outer mold 505. In some instances, the top outer mold 525 may be made out of a hard metal material (e.g., steel). Additionally, or alternatively, the top outer mold 525 may include one or more cavities 530 (e.g., a cavity 530-*a* and a cavity 530-*b*). The cavities 530 may be an empty space in the top outer mold 525 allowing for the filler to be injected into the filling gates 510 (e.g., a filling gate 510-*a* and a filling gate 510-*b*). That is, the cavities 530 may be located directly above the filling gates 510, where the bottom tip of each cavity 530 may align with an opening in a respective filling gate 510. CNC manufacturing may help control a size and a shape for each cavity 530, as well as any other aspect of the top outer mold 525.

In some cases, the molds structure 550 may include a molding tray 540 and a bolt 545 to help maintain the different components of the molds structure 550 (e.g., the bottom outer mold 505 and the top outer mold 525) in a fixed position. For example, the bolt 545 may ensure the top outer mold 525 and the bottom outer mold 505 are in a fixed position relative to the molding tray 540 throughout (e.g., during) the injection molding process.

As shown in the bottom portion of FIG. 5, the ring assembly 410 and the inner mold assembly 420 made up of the inner mold 405 and the inner mold pin 415 (as shown and described in FIG. 4) may be disposed within the molding assembly including the bottom outer mold 505 and the top outer mold 525.

In some cases, the injection molding process may include injecting a filler material through the one or more filling gates 510. For example, the injection molding process may be a vacuum molding process. For instance, a vacuum seal may be released allowing filler material to flow into the cavity 530-*a*, through the filling gates 510, and into the bottom outer mold 505. The filling gates 510 may be located around the outer circumferential surface of the ring assembly 410, allowing the filler material to cover one or more portions of the ring assembly 410 (e.g., the one or more electrical components 535 of the PCB 404). That is, the filling gates 510 may be located on an outer circumferential surface of the ring assembly 410 such that the filler/epoxy material flows from the outer circumferential surface of the ring assembly 410 toward the inner circumferential surface of the inner ring-shaped housing 402. In this regard, the molding process illustrated in FIG. 5 may secure the PCB 404 to the inner ring-shaped housing 402 and/or fill the apertures 406 of the inner ring-shaped housing 404. The electrical components 535 may include one or more of the PCB, optical components, and the battery. However, the molding process may inject more filling material than the available empty space surrounding the ring assembly 410.

In some cases, one or more venting gates 515 may allow a portion of the filler material to escape the mold structure 550. For example, any overflowing epoxy may escape through the venting gates 515. The venting gates 515 may also be referred to as overflow gates. The venting gates 515 may be located around the outer circumferential surface of the ring assembly 410, allowing the filler material to cover the empty spaces surrounding the ring assembly 410, and then escape through the venting gates 515. Thus, any "defects" or other imperfections formed by the filling gates 510 and/or venting gates 515 may be formed on an outer circumferential surface of the ring assembly 410.

In some cases, the filler material (e.g., a transparent epoxy material) may cover the ring assembly 410 during the molding process. For example, the filler material may secure the PCB 404 to the inner ring-shaped housing 402, fill the apertures 406 of the inner ring-shaped housing 402, and/or create an epoxy layer surrounding the ring assembly 410. Thus, the filler material may create a watertight seal such that the ring assembly 410 is waterproof. Additionally, or alternatively, the filler material may enable transmission of light through one or more apertures 406 of the inner ring-shaped housing 402. The result of the injection molding is a ring engine assembly (e.g., a molded engine unit) that may function as an operational ring (e.g., includes the necessary optical components, is waterproof, etc.) without an outer cover or shell. Further, any aesthetic deficiencies or imperfections, caused by the injection molding process (e.g., resulting from the filling gates 510 and the venting gates 515), in the ring engine assembly may be covered by the outer shell (e.g., alleviating the need to polish such imperfections).

As shown in FIG. 5, the filler material (e.g., transparent epoxy material) may flow out from the apertures within the inner ring-shaped housing 402 to fill one or more depressions 425 within the inner mold 405, thereby creating "domes" over the apertures of the inner ring-shaped housing 402. Conversely, in cases where the inner mold 405 does not include depressions 425, the inner mold 405 may be substantially flush with the inner circumferential surface of the inner ring-shaped housing 402, thereby creating a "smooth" inner circumferential surface of the ring (e.g., without domes).

Figure 6:
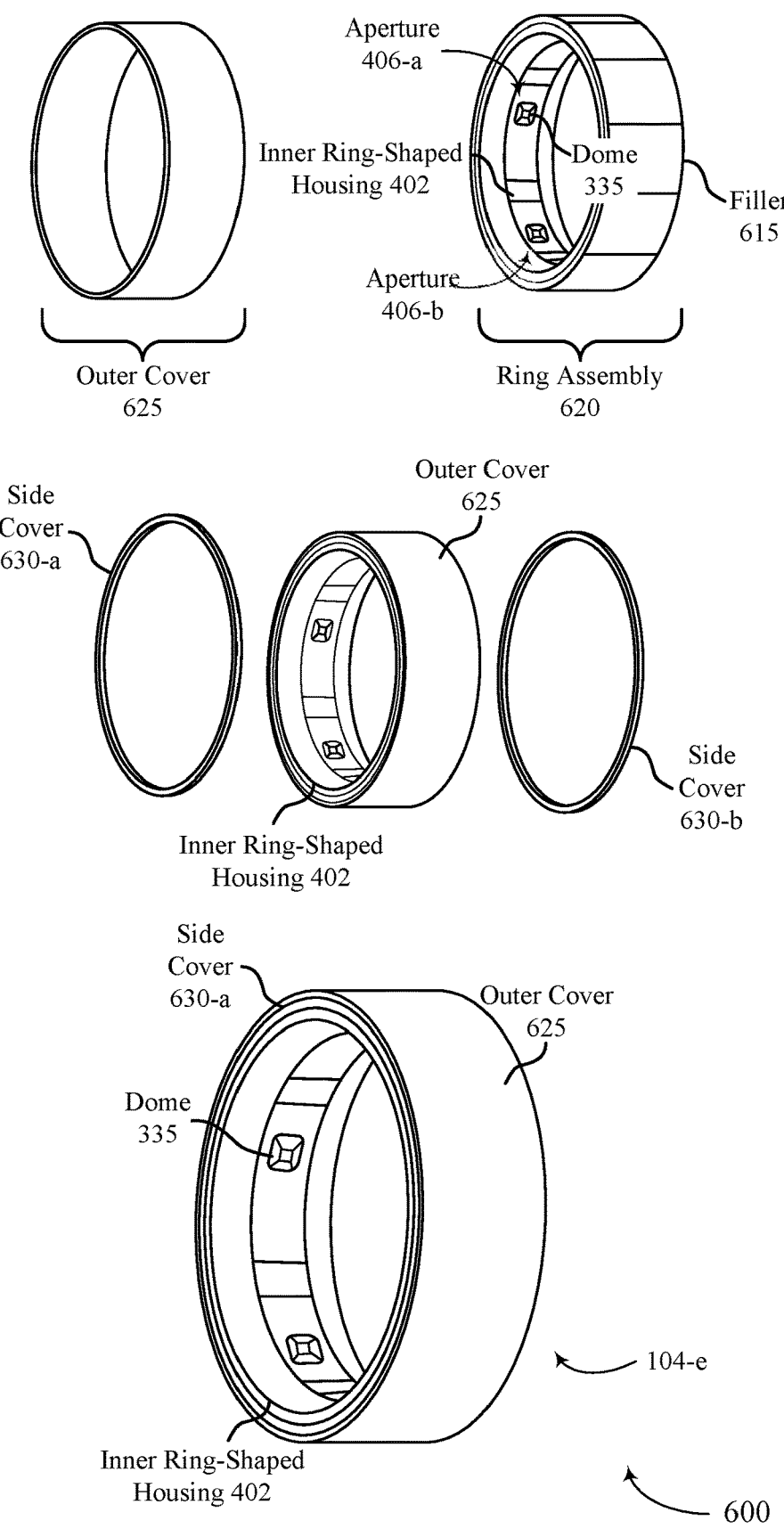
FIG. 6 shows an example of a system that supports techniques for manufacturing a wearable ring device in accordance with aspects of the present disclosure.

FIG. 6 shows an example of a system 600 that supports techniques for manufacturing a wearable ring device in accordance with aspects of the present disclosure. In other words, the system 600 may support techniques for a ring 104 to be manufactured "inside out," securing an outer cover 625 to an inner cover 605, including electrical components of the ring 104 (e.g., a wearable ring device 104-*e*), via multiple side covers 630, in a manner that allows for removing (e.g., replacing) a previous outer cover 625 and placing a different outer cover 625.

In particular, FIG. 6 illustrates a ring assembly 620 that results from the injection molding process shown and described in FIGS. 4 and 5. For example, as shown in FIG. 6, the ring assembly 620 may include the inner ring-shaped housing 402 described previously herein, as well as a filler 615 that was molded using the injection molding process shown and described in FIGS. 4 and 5. In this regard, the filler 615 (e.g., clear epoxy material) shown in FIG. 6 may substantially cover and seal the PCB 404 and/or battery of the wearable ring device to the inner ring-shaped housing 402. The inner ring-shaped housing 402 may define an inner circumferential surface of the ring assembly 620, and the filler 616 may define an outer circumferential surface of the ring assembly 620. As noted previously herein, in cases where the inner mold 405 included depressions 425, the ring assembly 620 may include one or more domes within the inner circumferential surface of the inner ring-shaped housing 402 that substantially fill and/or cover the one or more apertures 406. In this regard, the domes 335 may be made of the epoxy/filler 615 used to perform the injection molding process. The domes 335 may exhibit any shape, such as multi-faceted domes 335 (as shown in FIG. 6), curved domes 335 (e.g., spherical or elliptical-shaped domes 335), or both.

For instance, as described in FIGS. 4 and 5, the electrical components of the ring 104 may be attached to the inner ring-shaped housing 402 and placed into a mold. Subsequently, as shown in FIG. 5, a filler 615, such as a clear epoxy, may be injected into the mold to secure the electrical components (e.g., PCB 404, battery) of the wearable ring device to the inner ring-shaped housing 402. Additionally, the injection molding may cause the filler 615 to fill one or more apertures 406-*a*, 406-*b* of the inner ring-shaped housing 402, such that the one or more optical sensors of the PCB 404 may be aligned with the apertures 406 to enable data collection.

The result of injection molding process shown and described in FIGS. 4 and 5 may be the ring assembly 620 (e.g., the ring engine assembly) shown in FIG. 6. The ring assembly 620 may be an operational ring 104 without an outer cover 625 (e.g., outer ring-shaped housing). Subsequently, different outer covers 625 may be slid around the inner ring-shaped housing 402 (e.g., ring assembly 620) and the outer cover 625 may be secured to the inner ring-shaped housing 402 using side covers 630, such a side cover 630-*a* and a side cover 630-*b*, to finish the ring.

In some cases, as described previously herein, the battery may be coupled to the inner ring-shaped housing 402 prior to the molding process such that the filler 615 (e.g., epoxy) covers the battery and secures the battery to the inner ring-shaped housing 402. In additional or alternative implementations, the molding process may be performed without the battery, where the battery may be attached to the ring assembly 620 after the molding process such that the battery is positioned outside of (e.g., on top of) the filler 615 to enable the battery to be easily accessed and/or exchanged. For example, in cases where the molding process is performed without the battery, electrical leads may extend from the PCB 404 through the filler 615. In this example, the battery may be connected to the electrical leads, such that the electrical leads connect the battery to other components of the PCB 404 through the filler 615.

In some cases, the side covers 630 may secure (e.g., couple) the outer cover 625 to the ring assembly 620/inner ring-shaped housing 402. For instance, the side cover 630-*a* (e.g., a first ring-shaped fitting) may extend around the circumference of the wearable ring device 104-*e* on a first lateral side and the side cover 630-*b* (e.g., a second ring-shaped fitting) may extend around the circumference of the wearable ring device 104-*e* on a second lateral side. Thus, the wearable ring device 104-*e* may include the outer cover 625, the ring assembly 620 (e.g., the inner ring-shaped housing 402, the electrical components, and the filler 615) the side cover 630-*a*, and the side cover 630-*b*. The outer cover 625 may be secured to one or more portions of the ring assembly 620 (e.g., the inner ring-shaped housing 402, the filler 615, etc.), such that there are one or more gaps between the outer cover 625 and the ring assembly 620. The one or more gaps may enable communication (e.g., transmission and reception) of wireless signals into and out of the wearable ring device 104-*e*.

In some cases, securing the side covers 630 on to a wearable ring device 104-*e* may include pressing the side cover 630-*a* to the first lateral side and pressing the side cover 630-*b* to the second lateral side. Thus, the side cover 630-*a* and the side cover 630-*b* may lock (e.g., couple) the outer cover 625 to the ring assembly 620/inner ring-shaped housing 402. Additionally, or alternatively, the outer cover 625, the ring assembly 620, or both, may be pressed such that the outer cover 625 is concentric to the ring assembly 620.

In some cases, the outer cover 625 may be an exchangeable outer shell. That is, the side cover 630-*a*, the side cover 630-*b*, or both, may be removed from the wearable ring device 104-*e*. Subsequently, the outer cover 625 may be separated (e.g., removed) from the ring assembly 620. A new (e.g., different) outer cover 625 may be slid around the ring assembly 620 and then secured using the side covers 630. For instance, the new outer cover 625 may be a decorative or protective outer shell.

FIG. 7 shows a flowchart illustrating a method 700 that supports techniques for manufacturing a wearable ring device in accordance with aspects of the present disclosure. The operations of the method 700 may be implemented by a wearable device or its components as described herein. For example, the operations of the method 700 may be performed by a wearable device as described with reference to FIGS. 1 through 6. In some examples, a wearable device may execute a set of instructions to control the functional elements of the wearable device to perform the described functions. Additionally, or alternatively, the wearable device may perform aspects of the described functions using special-purpose hardware.

At 705, the method may include coupling a printed circuit board (PCB) to an inner ring-shaped housing comprising a plurality of apertures, wherein coupling the PCB to the inner ring-shaped housing comprises aligning a plurality of sensors of the PCB with the plurality of apertures. The operations of block 705 may be performed in accordance with examples as disclosed herein.

At 710, the method may include performing an injection molding process to fill a cavity between the inner ring-shaped housing and a surface of a mold with a filler material, wherein the filler material is configured to bind the PCB to the inner ring-shaped housing, and wherein performing the injection molding process comprises filling at least a portion of the plurality of apertures of the inner ring-shaped housing with the filler material. The operations of block 710 may be performed in accordance with examples as disclosed herein.

At 715, the method may include coupling an outer ring-shaped housing to the inner ring-shaped housing, the filler material, or both, following a completion of the injection molding process, wherein an inner circumferential surface of the outer ring-shaped housing at least partially surrounds an outer circumferential surface of the filler material following the injection molding process. The operations of block 715 may be performed in accordance with examples as disclosed herein.

It should be noted that the methods described above describe possible implementations, and that the operations and the steps may be rearranged or otherwise modified and that other implementations are possible. Furthermore, aspects from two or more of the methods may be combined.

A method for manufacturing a wearable ring device by an apparatus is described. The method may include coupling a printed circuit board (PCB) to an inner ring-shaped housing comprising a plurality of apertures, wherein coupling the PCB to the inner ring-shaped housing comprises aligning a plurality of sensors of the PCB with the plurality of apertures, performing an injection molding process to fill a cavity between the inner ring-shaped housing and a surface of a mold with a filler material, wherein the filler material is configured to bind the PCB to the inner ring-shaped housing, and wherein performing the injection molding process comprises filling at least a portion of the plurality of apertures of the inner ring-shaped housing with the filler material, and coupling an outer ring-shaped housing to the inner ring-shaped housing, the filler material, or both, following a completion of the injection molding process, wherein an inner circumferential surface of the outer ring-shaped housing at least partially surrounds an outer circumferential surface of the filler material following the injection molding process.

In some examples of the method, the injection molding process forms a ring assembly comprising an inner circumferential surface defined at least partially by the inner ring-shaped housing, and an outer circumferential surface defined at least partially by the filler material.

In some examples of the method, performing the injection molding process may include operations, features, means, or instructions for injecting the filler material through one or more fill gates of the mold, wherein the one or more fill gates may be positioned proximate to the outer circumferential surface of the ring assembly.

In some examples of the method, one or more vent gates of the mold allow at least a portion of the filler material to escape the mold and the one or more vent gates may be positioned proximate to the outer circumferential surface of the ring assembly.

In some examples of the method, the filler material may be configured to create a watertight seal such that the ring assembly may be waterproof.

In some examples of the method, coupling the PCB to the inner ring-shaped housing may include operations, features, means, or instructions for coupling a battery of the wearable ring device to the inner ring-shaped housing, wherein the injection molding process may be configured to bind the battery to the inner ring-shaped housing.

In some examples of the method, the PCB comprises one or more electrical leads configured to electrically couple the plurality of sensors with a battery of the wearable ring device and the method, apparatuses, and non-transitory computer-readable medium may include further operations, features, means, or instructions for coupling the battery to the one or more electrical leads following the completion of the injection molding process.

In some examples of the method, the inner ring-shaped housing defines a passage configured to at least partially surround a finger of a user when the wearable ring device may be worn by the user and the method, apparatuses, and non-transitory computer-readable medium may include further operations, features, means, or instructions for inserting a mold pin into the passage of the inner ring-shaped housing, wherein the mold pin may be configured to control an amount of filler material that flows out of the cavity through the plurality of apertures of the inner ring-shaped housing during the injection molding process.

In some examples of the method, a surface of the mold pin may be substantially flush with an inner circumferential surface of the inner ring-shaped housing during the injection molding process such that the filler material within the plurality of apertures may be substantially flush with the inner circumferential surface of the inner ring-shaped housing following a completion of the injection molding process.

Some examples of the method may further include operations, features, means, or instructions for coupling the outer ring-shaped housing to the inner ring-shaped housing using a first ring-shaped fitting and a second ring-shaped fitting, the first ring-shaped fitting and the second ring-shaped fitting extending around a circumference of the wearable ring device on a first lateral side and a second lateral side of the wearable ring device, respectively.

In some examples of the method, coupling the outer ring-shaped housing to the inner ring-shaped housing using the first ring-shaped fitting and the second ring-shaped fitting may include operations, features, means, or instructions for pressing the first ring-shaped fitting to the first lateral side of the wearable ring device and pressing the second ring-shaped fitting to the second lateral side of the wearable ring device.

In some examples of the method, the outer ring-shaped housing may be removably coupled to the inner ring-shaped housing, the filler material, or both.

In some examples of the method, coupling the PCB to the inner ring-shaped housing may include operations, features, means, or instructions for engaging a first set of locating components of the PCB with a second set of locating components of the inner ring-shaped housing to maintain the PCB in a radial orientation of a plurality of radial orientations relative to the inner ring-shaped housing, wherein aligning the plurality of sensors of the PCB with the plurality of apertures may be based at least in part on the engaging.

In some examples of the method, the filler material comprises a transparent epoxy material that may be configured to enable transmission of light through the plurality of apertures.

In some examples of the method, the inner ring-shaped housing comprises a first metallic material and the outer ring-shaped housing comprises a second metallic material that may be the same or different compared to the first metallic material.

In some examples of the method, the outer ring-shaped housing may be coupled to the inner ring-shaped housing, the filler material, or both, such that there may be one or more gaps between the inner ring-shaped housing and the outer ring-shaped housing and the one or more gaps enable transmission and reception of wireless signals into and out of the wearable ring device.

Some examples of the method may further include operations, features, means, or instructions for coupling the mold to a molding tray, wherein the mold may be in a fixed position relative to the molding tray during the injection molding process.

In some examples of the method, coupling the outer ring-shaped housing to the inner ring-shaped housing, the filler material, or both may include operations, features, means, or instructions for pressing the outer ring-shaped housing, the inner ring-shaped housing, or both, such that the outer ring-shaped housing may be concentric to the inner ring-shaped housing.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A method for manufacturing a wearable ring device, comprising:

coupling a printed circuit board (PCB) to an inner ring-shaped housing comprising one or more apertures, wherein coupling the PCB to the inner ring-shaped housing comprises aligning a plurality of sensors of the PCB with the one or more apertures;

performing an injection molding process to fill a cavity between the inner ring-shaped housing and a surface of a mold with a filler material, wherein the filler material is configured to bind the PCB to the inner ring-shaped housing, and wherein performing the injection molding process comprises filling at least a portion of the one or more apertures of the inner ring-shaped housing with the filler material; and coupling an outer ring-shaped housing to the inner ring-shaped housing, the filler material, or both, following a completion of the injection molding process, wherein an inner curved surface of the outer ring-shaped housing at least partially surrounds an outer curved surface of the filler material following the injection molding process.

2. The method of claim 1, wherein the injection molding process forms a ring assembly comprising an inner surface defined at least partially by the inner ring-shaped housing, and the outer curved surface defined at least partially by the filler material.

3. The method of claim 2, wherein performing the injection molding process comprises:

injecting the filler material through one or more fill gates of the mold, wherein the one or more fill gates are positioned proximate to the outer curved surface of the ring assembly.

4. The method of claim 3, wherein one or more vent gates of the mold allow at least a portion of the filler material to escape the mold, wherein the one or more vent gates are positioned proximate to the outer curved surface of the ring assembly.

5. The method of claim 2, wherein the filler material is configured to create a watertight seal such that the ring assembly is waterproof.

6. The method of claim 1, wherein coupling the PCB to the inner ring-shaped housing comprises:

coupling a battery of the wearable ring device to the inner ring-shaped housing, wherein the injection molding process is configured to bind the battery to the inner ring-shaped housing.

7. The method of claim 1, wherein the PCB comprises one or more electrical leads configured to electrically couple the plurality of sensors with a battery of the wearable ring device, wherein the one or more electrical leads extend out from the cavity during the injection molding process such that the one or more electrical leads extend from the filler material following a completion of the injection molding process, the method further comprising:

coupling the battery to the one or more electrical leads following the completion of the injection molding process.

8. The method of claim 1, wherein the inner ring-shaped housing defines a passage configured to at least partially surround a finger of a user when the wearable ring device is worn by the user, the method further comprising:

inserting a mold pin into the passage of the inner ring-shaped housing, wherein the mold pin is configured to control an amount of filler material that flows out of the cavity through the one or more apertures of the inner ring-shaped housing during the injection molding process.

9. The method of claim 8, wherein a surface of the mold pin is substantially flush with an inner curved surface of the inner ring-shaped housing during the injection molding process such that the filler material within the one or more apertures is substantially flush with the inner curved surface of the inner ring-shaped housing following a completion of the injection molding process.

10. The method of claim 1, further comprising:

coupling the outer ring-shaped housing to the inner ring-shaped housing using a first ring-shaped fitting and a second ring-shaped fitting, the first ring-shaped fitting and the second ring-shaped fitting extending around a circumference of the wearable ring device on a first lateral side and a second lateral side of the wearable ring device, respectively.

11. The method of claim 10, wherein coupling the outer ring-shaped housing to the inner ring-shaped housing using the first ring-shaped fitting and the second ring-shaped fitting further comprises:

pressing the first ring-shaped fitting to the first lateral side of the wearable ring device; and pressing the second ring-shaped fitting to the second lateral side of the wearable ring device.

12. The method of claim 1, wherein the outer ring-shaped housing is removably coupled to the inner ring-shaped housing, the filler material, or both.

13. The method of claim 1, wherein coupling the PCB to the inner ring-shaped housing comprises:

engaging a first set of locating components of the PCB with a second set of locating components of the inner ring-shaped housing to maintain the PCB in a radial orientation of a plurality of radial orientations relative to the inner ring-shaped housing, wherein aligning the plurality of sensors of the PCB with the one or more apertures is based at least in part on the engaging.

14. The method of claim 1, wherein the filler material comprises a transparent epoxy material that is configured to enable transmission of light through the one or more apertures.

15. The method of claim 1, wherein the inner ring-shaped housing comprises a first metallic material, and wherein the outer ring-shaped housing comprises a second metallic material that is the same or different compared to the first metallic material.

16. The method of claim 15, wherein the outer ring-shaped housing is coupled to the inner ring-shaped housing, the filler material, or both, such that there are one or more gaps between the inner ring-shaped housing and the outer ring-shaped housing, wherein the one or more gaps enable transmission and reception of wireless signals into and out of the wearable ring device.

17. The method of claim 1, further comprising:

coupling the mold to a molding tray, wherein the mold is in a fixed position relative to the molding tray during the injection molding process.

18. The method of claim 1, wherein coupling the outer ring-shaped housing to the inner ring-shaped housing, the filler material, or both, comprises:

pressing the outer ring-shaped housing, the inner ring-shaped housing, or both, such that the outer ring-shaped housing is concentric to the inner ring-shaped housing.

19. The method of claim 1, wherein the mold comprises one or more depressions that are aligned with the one or more apertures within the inner ring-shaped housing, wherein the filler material flows out of the one or more apertures during the injection molding process to fill the one or more depressions and create one or more domes that substantially cover and fill the one or more apertures.

* * * * *